United States Patent [19]

Hruby et al.

[11] Patent Number: 4,684,620

[45] Date of Patent: Aug. 4, 1987

[54] CYCLIC POLYPEPTIDES HAVING MU-RECEPTOR SPECIFICITY

[75] Inventors: Victor J. Hruby; John T. Pelton, both of Tucson, Ariz.

[73] Assignee: Gibson-Stephens Neuropharmaceuticals, Inc., Tucson, Ariz.

[21] Appl. No.: 647,184

[22] Filed: Sep. 4, 1984

[51] Int. Cl.$^4$ .................. A61K 37/43; C07K 7/12; C07K 7/06

[52] U.S. Cl. ................. 514/11; 530/809; 530/329; 530/302

[58] Field of Search ............. 260/112.55; 514/806, 514/11; 530/809, 329, 302

[56] References Cited

U.S. PATENT DOCUMENTS 4,282,143  8/1981  Sarantakis .............. 260/112.55
4,395,403  7/1983  Bauer et al. ............ 260/112.55
4,496,543  1/1985  Bauer et al. ............ 260/112.55

OTHER PUBLICATIONS

Maurer et al., "Opiate Antagonistic Properties of an Octapeptide Somatostatin Analog," *Proc. Natl. Acad. Sci. USA* 79, 4815 (1982).

*Primary Examiner*—Delbert R. Phillips

[57] ABSTRACT

Novel compounds which are capable of binding with enhanced specificity to the mu opioid receptor are disclosed. The compounds are analogs of somatostain and have the formula:

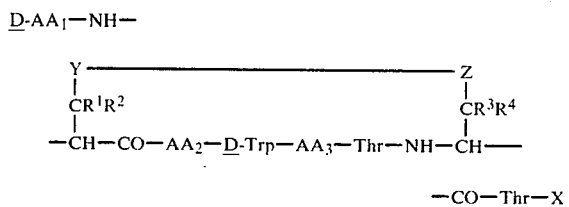

wherein

X is $CONH_2$ or $CH_2OH$;

Y and Z are independently sulfur or $CH_2$;

$R^1$ and $R^2$, which may be the same or different, are hydrogen, methyl, ethyl, cyclopentamethylene, or a lower alkyl group having five or less carbon atoms;

$R^3$ and $R^4$, which may be the same or different, are hydrogen, methyl, ethyl, cyclopentamethylene, or a lower alkyl group having five or less carbon atoms, provided, however, that $R^1$, $R^2$, $R^3$, and $R^4$ may not all be hydrogen;

$AA_1$ is Phe, D-Phe, phenyl-Gly, D-phenyl-Gly, Tyr, D-Tyr, L-1-Naphthylalanine, D-1-Naphthylalanine, or D-Phe(4-Me);

$AA_2$ is Tyr, Phe, Tyr(OMe), Phe(4-Me), Tyr(OEt), or Phe(4-Et); and $AA_3$ is Lys, Arg, Orn or homo-Arg.

The novel compounds have antagonist activity and may be used to induce pharmacological or therapeutic effects in humans and other animals.

16 Claims, No Drawings

CYCLIC POLYPEPTIDES HAVING MU-RECEPTOR SPECIFICITY

The Government has rights to this invention pursuant to Grant Nos. AM-21085 and AM-06936 awarded by the Department of Health and Human Services.

This invention relates to compounds which are cyclic polypeptides having mu opiate receptor specificity. The compounds ate believed to be useful in the treatment of opiate addiction, irritable bowel syndrome and schizophrenia. The invention also relates to a method of inducing pharmacological manifestations associated with mu receptor antagonist activity by administering a safe and effective amount of the mu receptor specific compounds.

BACKGROUND OF THE INVENTION

Receptors are those entities on or in a cell which recognize and bind drugs, hormones or other specific substances. After binding with the receptor, these substances may act to initiate or block biochemical and physiological sequences. Such initiation or blockage is often referred to as transduction. Thus, the receptor binding properties of a particular compound dictate the physiological effects that a particular compound will produce.

Opiate receptors are responsible for mediating analgesia. There are several known opiate receptor types, among the known opiate receptor subtypes are the mu, delta and kappa receptors. All three of these receptor subtypes are known to mediate analgesia, but each differs considerably in their other pharmacological effects. For instance, mu receptors additionally mediate respiratory depression and inhibit gastrointestinal transit.

Compounds structurally capable of binding at receptor sites may induce a variety of biological effects, all of which are useful in attaining a variety of pharmacological and therapeutic effects. For example, antagonists bind to the receptor but do not transduce the biological system to produce a response. Thus, antagonists can block the action of naturally occurring hormones and have great therapeutic value.

Somatostatin is a cyclic tetradecapeptide which is known to interact with numerous receptor systems, including the opiate receptors. Natural occurring somatostatin has the formula:

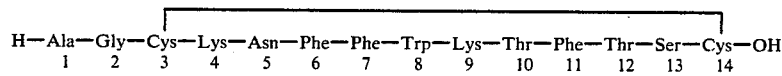

Peptides, such as somatostatin, are identified by amino acid sequence using established abbreviations. For example, as used herein, "Ala" stands for Alanine, "Gly" stands for Glycine, "Cys" stands for Cysteine, "Lys" stands for Lysine, "Asn" stands for Asparagine, "Phe" stands for Phenylalanine, "Trp" stands for Tryptophan, "Thr" stands for Threonine, "Arg" stands for Arginine and "Pen" stands for Penicillamine. Polypeptide derivatives in which one or more of the amino acids have been replaced by another amino acid are often described by reference to the basic compound and the position and the nature of the substitution. The position of substitution is usually identified by reference to the number of the amino acid in the sequence starting with the amino acid at the amino terminus of the peptide chain. For example, the somatostatin analog,

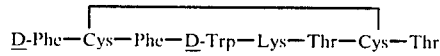

is written as

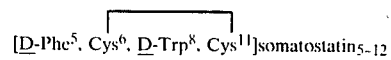

signifying the 5–12 amino acid residues of naturally occurring somatostatin. Additionally, amino acids may exist as stereoisomers in both L and D configurations.

Somatostatin is believed to exert a variety of hormonal actions such as inhibition of growth hormone release from the pituitary gland, inhibition of insulin release in the pancreas, inhibition of glucagon release in the pancreas, and interact with opiate receptors. Additionally, it has been reported that

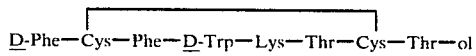

acts as a mu opioid antagonist. See Maurer, R., Gaehwiler, B. H., Buescher, H. H., Hill, R. C. and Roemer, D., *Proc. Natl. Acad. Sci. USA* 79, 4815–4817 (1982), which is herein specifically incorporated by reference.

SUMMARY OF THE INVENTION

The present invention provides novel compounds which have greatly increased specificity for the mu opiate receptor (hereinafter sometimes referred to as "mu receptor specificity"). The compounds are a series of cyclic, conformationally restricted polypeptides which are analogs of the naturally occurring peptide, somatostatin. More specifically, preferred compounds of the present invention are octapeptides and are somatostatin analogs of the 5–12 sequence. The novel compounds function as mu antagonists and may be used to induce pharmacological or therapeutic effects corresponding to mu antagonist activity in humans and other animals. The compounds may be used as analgesic inhibitors to block morphine and other opiate addictions, may be useful in the treatment of schizophrenia, irritable bowel disease, diarrhea and in the regulation of body temperature.

In accordance with the present invention, there are provided polypeptides of the formula:

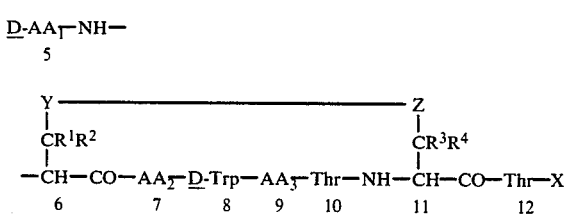

wherein
X is $CONH_2$ or $CH_2OH$;
Y and Z are independently sulfur or $CH_2$;
$R^1$ and $R^2$, which may be the same or different, are hydrogen, methyl, ethyl, cyclopentamethylene, or a lower alkyl group having five or less carbon atoms;
$R^3$ and $R^4$, which may be the same or different, are hydrogen, methyl, ethyl, cyclopentamethylene, or a lower alkyl group having five or less carbon atoms, provided, however, that $R^1$, $R^2$, $R^3$, and $R^4$ may not all be hydrogen;
$AA_1$ is Phe, D-Phe, Phenylglycine, D-Phenylglycine, Tyr, D-Tyr, L-1-Naphthylalanine, D-1-Naphthylalanine, or D-Phe(4-Me);
$AA_2$ is Tyr, Phe, Tyr(OMe), Phe(4-Me), Tyr(OEt), or Phe(4-Et); and
$AA_3$ is Lys, Arg, Orn or homo-Arg. All amino acid residues which have chiral centers are of the L configuration except for those residues in position 5 which can be either the D or L configuration and position 8 which is in the D configuration. A preferred group of compounds which are highly mu specific antagonists have the formula:

$$\begin{array}{c} S\text{\textemdash}\text{\textemdash}\text{\textemdash}\text{\textemdash}\text{\textemdash}\text{\textemdash}\text{\textemdash}\text{\textemdash}\text{\textemdash}S \\ | \quad\quad\quad\quad\quad\quad\quad | \\ \underline{D}\text{-Phe}\text{\textemdash}\text{Cys}\text{\textemdash}AA_2\text{\textemdash}\underline{D}\text{-Trp}\text{\textemdash}\text{Lys}\text{\textemdash}\text{Thr}\text{\textemdash}\text{Pen}\text{\textemdash}\text{Thr}\text{\textemdash}X \end{array}$$

wherein
$AA_2$ is Tyr, Phe, Tyr(OMe), Phe(4-Me), Tyr(OEt), or Phe(4-Et); and
X is $CONH_2$ or $CH_2OH$.

Particularly preferred compounds include:

$\underline{D}$-Phe—Cys—Tyr—$\underline{D}$-Trp—Lys—Thr—Pen—Thr—$NH_2$ and $\underline{D}$-Phe—Cys—Phe—$\underline{D}$-Trp—Lys—Thr—Pen—Thr—$NH_2$ Additional objects and advantages of the invention will be set forth in part in the description which follows, and in part will be obvious from the description, or may be learned from the practice of the invention. The objects and advantages may be realized and obtained by means of the instrumentalities and combinations particularly pointed out in the appended claims.

DESCRIPTION OF THE PREFERRED EMBODIMENTS

Reference will now be made in detail to the presently preferred embodiments of the invention, which together with the following examples, serve to explain the principles of the invention.

As noted above, the present invention relates to polypeptides of the formula:

$\underline{D}$-$AA_1$—NH—

$$\begin{array}{c} Y\text{\textemdash}\text{\textemdash}\text{\textemdash}\text{\textemdash}\text{\textemdash}\text{\textemdash}\text{\textemdash}Z \\ | \quad\quad\quad\quad\quad\quad\quad | \\ CR^1R^2 \quad\quad\quad\quad\quad CR^3R^4 \\ | \quad\quad\quad\quad\quad\quad\quad | \\ \text{\textemdash}CH\text{\textemdash}CO\text{\textemdash}AA_2\text{\textemdash}\underline{D}\text{-Trp}\text{\textemdash}AA_3\text{\textemdash}\text{Thr}\text{\textemdash}NH\text{\textemdash}CH\text{\textemdash}\text{\textemdash} \end{array}$$

—CO—Thr—X wherein
X is $CONH_2$ or $CH_2OH$;
Y and Z are independently sulfur or $CH_2$;
$R^1$ and $R^2$, which may be the same or different, are hydrogen, methyl, ethyl, cyclopentamethylene, or a lower alkyl group having five or less carbon atoms;
$R^3$ and $R^4$, which may be the same or different, are hydrogen, methyl, ethyl, cyclopentamethylene, or a lower alkyl group having five or less carbon atoms, provided, however, that $R^1$, $R^2$, $R^3$, and $R^4$ may not all be hydrogen;
$AA_1$ is Phe, D-Phe, Phenylglycine, D-Phenylglycine, Tyr, D-Tyr, L-1-Naphthylalanine, D-1-Naphthylalanine, or D-Phe(4-Me);
$AA_2$ is Tyr, Phe, Tyr(OMe), Phe(4-Me), Tyr(OEt), or Phe(4-Et); and
$AA_3$ is Lys, Arg, Orn or homo-Arg.

As noted above, a preferred group of compounds within the present invention are highly mu receptor antagonists having the formula:

$$\begin{array}{c} S\text{\textemdash}\text{\textemdash}\text{\textemdash}\text{\textemdash}\text{\textemdash}\text{\textemdash}\text{\textemdash}\text{\textemdash}\text{\textemdash}S \\ | \quad\quad\quad\quad\quad\quad\quad | \\ CH_2 \quad\quad\quad\quad\quad C(CH_3)_2 \\ | \quad\quad\quad\quad\quad\quad\quad | \\ \underline{D}\text{-Phe}\text{\textemdash}\text{Cys}\text{\textemdash}AA_2\text{\textemdash}\underline{D}\text{-Trp}\text{\textemdash}\text{Lys}\text{\textemdash}\text{Thr}\text{\textemdash}\text{Pen}\text{\textemdash}\text{Thr}\text{\textemdash}X \end{array}$$

wherein
$AA_2$ is Tyr, Phe, Tyr(OMe), Phe(4-Me), Tyr(OEt), or Phe(4-Et); and
X is $CONH_2$ or $CH_2OH$.

Particularly preferred compounds include:

$\underline{D}$-Phe—Cys—Tyr—$\underline{D}$-Trp—Lys—Thr—Pen—Thr—$NH_2$ and $\underline{D}$-Phe—Cys—Phe—$\underline{D}$-Trp—Lys—Thr—Pen—Thr—$NH_2$.

The polypeptides of the present invention are cyclized compounds having high mu receptor selectivity and displaying pharmacological activity. A preferred group of compounds display antagonist activity. It is believed that these features can be attributed to the presence of either some or all of the following: a Cysteine amino acid residue in position 6, a Tyrosine amino acid residue in position 7, a Penicillamine amino acid residue at position 11, and/or a carboxamide terminal at position 12. The compounds are also conformationally constrained to enhance their mu receptor binding affinities.

Since the mu opiate receptors mediate analgesia as well as mediate respiratory depression and inhibit gastrointestinal transit it is believed that the compounds of the present invention, which are highly mu specific are useful in treating opiate effects, treating mental and central nervous system disorders, treating digestive disease, and treating eating disorder such as excessive appetite, gluttony and anorexia. (See generally, Malek-Ahmadi, P., and Callen, K. E., Gen. Pharmac. 11, 149–151 (1980) and Barchas, J. D., Berger, P. A., Watson, S. J., Huda, A., and Li, C. H., Neural Pept. and Neuronal Comm., 447–453 (1980) which are herein specifically incorporated by reference.

Clinicians are often hesitant to prescribe opiates as pain killers because of the associated danger of respiratory depression. The compounds of the present invention, because of their high mu receptor selectivity, antagonize the respiratory depression side effects resulting from opiates. Thus, opiates can be prescribed as effective pain killers and the undesirable side effects associated with their use can be minimized.

It is also believed that the compounds of the present invention are useful in the treatment of gastrointestinal disorders. Some gastrointestinal disorders are the result of an over abundance of natural opiates in the gut. If an opiate antagonist is administered the binding of the natural opiates to the mu receptors would be prevented. In other words, a highly mu receptor specific antagonist would improve gastrointestinal transit.

The compounds of the present invention were tested for their activity and these results are summarized in Tables 1, 2 and 3. Table 1 compares the binding properties at the mu opioid receptor of the compounds of the present invention with somatostatin. The increased mu receptor specificity of the compounds of the present invention is shown in Table 1. Specifically,

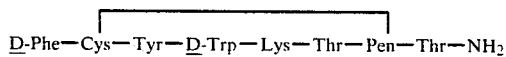

in 7,800 times more potent at the mu opioid receptor than somatostatin.

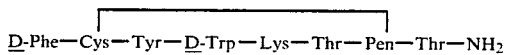

has an $IC_{50}$ value of 3.5 nM whereas somatostatin has an IC50 value of 27,361 nM.

Additionally, the compounds of the invention were compared with a somatostatin 7-10 fragment analog, a somatostatin analog (CGP 23,996: having the formula des-Ala$^1$,Gly$^2$-desamino-Cys3-[Tyr$^{11}$]-dicarba$^{3,14}$-somatostatin) and morphine-HCl.

Table 2 compares the inhibition of somatostatin and the compounds of the present invention to $^{125}$I CGP 23,996 in rat brain membranes. The compounds of the present invention were less potent than somatostatin. These tests, therefore, demonstrate that the somatostatin analogs of the present invention are extremely mu selective.

Table 3 demonstrates the relative antagonizing effects at mu opioid receptors of a compound of the present invention.

Preparation of compounds within the scope of the present invention appear in the following examples.

EXAMPLE 1

Preparation of D-Phe—Cys—Tyr—D-Trp—Lys—Thr—Pen—Thr

N-α-tert-Butyloxycarbonyl-0-benzylL-Threonine, 2.2 g (7.2 mmol) were reacted with 10 g chloromethylated copoly[styrene-1%-divinyl benzene]beads (Lab Systems, 0.71 meq Cl/g resin) in the presence of cesium bicarbonate, 1.39 g, 7.2 mmol in 30 ml dry dimethylformamide (hereinafter DMF) for 48 hours at 60° C. with constant overhead mechanical stirring. The resin was then thoroughly washed with DMF, 90:10 DMF-water, DMF, ethanol, DMF and methylene chloride. The resin was dried in vacuo to a constant weight and a small sample (4.2 mg resin) was hydrolyzed with 1 ml 50:50, 12 N HCl-propionic acid for 24 hours at 110° C. The hydrolyzate was dried in vacuo, dissolved in a citrate buffer having a pH of 2.2 (0.2 M) and then assayed by amino acid analyzer for Threonine. Substitution of the amino acid amounted to 0.35 mmoles per gram of resin.

The resin, 1.5 g, 0.52 mmol N-α-tert-butyloxycarbonyl-0-benzyl-L-Threonine-resin was placed in a 45 ml reaction vessel of a Model 250 Vega automated peptide synthesizer and washed three times with 20 ml of methylene chloride and then allowed to swell overnight in 25 ml of methylene chloride. The protecting t-BOC group was cleaved with 20 ml of 50% trifluoroacetic acid in methylene chloride with 3% anisole for a 20-minute reaction time. The resin was then washed with methylene chloride, 3 times with 20 ml for 3 minutes. The resin was then neutralized by washing 2 times with 20 ml of 10% diisopropylethylamine in methylene chloride followed by three more washes with methylene chloride, as above. To 0.55 g (1.56 mmol), of N-α-tert-butyloxycarbonyl-O-p-methylbenzyl-L-Penicillamine in approximately 15 ml of methylene chloride, all at 4° C., was added 16 g, (0.78 mmol) dicyclohexylcarbodiimide (hereinafter DCC) and the mixture was allowed to stand in an ice bath for approximately 20–30 minutes to form the symmetrical anhydride of the protected amino acid. The material was then filtered (to remove the precipitated dicyclohexylurea) directly into the reaction vessel and allowed to react for 30 minutes with continuous shaking. The resin was washed with methylene chloride, absolute ethanol, and methylene chloride, 20 ml of each 3 times for 3 minutes, respectively. Approximately 1 mg of resin was then removed and tested with two drops each of a 10% solution of ninhydrin in ethanol, pyridine, and phenol (80 g in 20 ml ethanol), and heated in an oil bath at 100° C. for 4 minutes to determine if the coupling reaction had gone to completion. The coupling reaction with the preformed symmetrical anhydride was then repeated, if necessary. The t-BOC group was removed from the Penicillamine residue with 20 ml of 50% trifluoroacetic acid (hereinafter TFA) in methylene chloride with 3% anisole, washed and neutralized with diisopropylethylamine in methylene chloride, as before.

In a similar manner, 0.48 g, 1.56 mmol N-α-tert-butyloxycarbonyl-0-benzyl-L-Threonine was activated with 0.16 g (0.78 mmol) of DCC and coupled to the Penicillamine residue, deprotected, and neutralized. Next, 0.70 g (1.56 mmol) of N-α-tert-butyloxycarbonyl-N-ε-2,4-dichlorobenzyloxycarbonyl-L-Lysine was activated and coupled to Threonine. The steps of deprotection (cleavage of the t-BOC group only) with TFA, washing, neutralization with diisopropylethylamine, washing and coupling with the preformed symmetrical anhydride were repeated for each amino acid residue in an identical manner except that after Tryptophan was attached to the peptide, the TFA solution was modified to contain 40% TFA, 3% anisole, 10% ethanedithiol and 5% dimethyl sulfide in methylene chloride and the reaction vessel was thoroughly purged with nitrogen after the TFA solution had been added. Thus, Nα-t-BOC-D-Trp was incorporated into the growing peptide without additional side-chain protection. The protection scheme for the remaining amino acids was: t-BOC-L-Tyr(2,6-Cl$_2$Bzl), t-BOC-L-Cys(S-P CH$_3$Bzl) and t-BOC-D-Phe.

After the synthesis of the peptide on the resin was completed, the material was removed from the vessel, dried in vacuo and the peptide cleaved from the resin support by anhydrous liquid HF (10 ml/g resin) containing 10% anisole at 4° C. for 45 minutes. The peptide was extracted with 50% acetic acid, which had previously been purged with nitrogen, until the extract was no longer positive to the ninhydrin test, and then lyophilized. The white powder was dissolved in a minimum amount of degassed DMF (about 30 ml) and then diluted with approximately 1700 ml of 0.1% acetic acid. The pH was adjusted to 8.5 with 2.5 N ammonium hydroxide and the peptide was then oxidized with an excess of 0.01 M $K_3Fe(CN)_6$. The resulting yellow solution was stirred for 30 minutes while maintaining the pH at 8.5. The pH was then lowered to 4.0 with glacial acetic acid and the ferro- and ferricyanide ions were removed from the solution by addition of 20 ml settled anion exchange resin (Rexyn 203 or Bio Rad 3X4A, $Cl^-$ form). The mixture was stirred at room temperature for one hour, filtered and the aqueous solution evaporated to about 300–400 ml by rotary evaporation in vacuo at 30°–40° C. The concetrated solution was the lyophilized to yield a salty, white powder.

The dry powder was dissolved in a minimum amount of 30% acetic acid (about 25 ml) and was applied to a Sephadex G-15 column (2.6×60 cm). Gel filtration (flow, 6.8 ml/hour) yielded several peaks with the major Ehrlich and UV ($\lambda=280$) positive peak centered at about 480 ml. The major peak was collected and lyophilized to yield a white, fluffy powder which appeared to be substantially (80%) pure by HPLC ($k'=3.0$, Vydac 218TP15-16 $C_{18}$ RP column, 25 cm×4.6 mm, 0.1% trifluoroacetic acid, $CH_3CN$, 78:22, flow: 2.5 ml/min, $\lambda$214 nm). The material was dissolved in a small amount of acetate buffer (20 mM sodium acetate, pH 3.5) and applied to a SP-Sephadex cation exchange column (2.4×20 cm) previously equilibrated with the acetate buffer. The peptide was eluted with a linear salt gradient from 0.3 M to 1.2 M NaCl. The major peak, eluting at approximately 0.8 M NaCl, was collected and lyophilized. The material was then dissolved in a minimum amount of 30% acetic acid and desalted on a Sephadex G-15 column (2.6×60 cm) with 5% acetic acid. The major peak, again eluting at about 480 ml, was collected and lyophilized. The dry powder was dissolved in the upper phase of the solvent system 1-butanol, pyridine, benzene, 0.1% acetic acid (60:10:20'90) and placed on a Sephadex G-25 (block polymerizate) column which had been equilibrated with the upper and lower phases according to the method of D. Yamashiro, *Nature* 201:76–78, 1964, which is herein specifically incorporated by reference. Fractions (approximately 6 ml) were monitored by UV and the Ehrlich test. A single major peak was obtained (Rf=0.24) which was collected, diluted with 0.2 N acetic acid and lyophilized. Final gel filtration on Sephadex G-15 with 5% acetic acid gave the pure peptide, 91 mg (16% yield), as a white, fluffy powder; amino acid analysis: Phe (1.04); Tyr (1:00); Lys (1.06); Thr (1.85); Cys, as cysteic acid (0.94); Pen and Trp not determined; $\epsilon\lambda=278=6700$ $M^{-1}cm^{-1}$; $[M+H]^+=1076.5$ (calc 1076.4); TLC 0.23 (A); 0.68 (B); 0.63 (C); 0.82 (D); 0.53 (E); Paper Electrophoresis, pH 2.2 (11.3 cm); pH 5.6 (6.8 cm); HPLC, $k'=3.0$ (F); 3.8 (G); 4.9 (H); 2.2 (I); Partition Coefficient, Octanol-Water, log P=0.70;

The TLC solvent systems were: (A) butanol, acetic acid, water, 4:1:5 (upper phase); (B) butanol, acetic acid, water, pyridine, 15:3:10:12; (C) butanol, acetic acid, water, pyridine, 6:1.2:4.8:6; (D) isopropyl alcohol, ammonia, water, 3:1:1; (E) butanol, pyridine, 0.1% acetic acid, 5:3:11 (upper phase). Paper Electrophoresis: 450 volts for 90 min at 4° C., peptides moved towards the cathode, reported as cm from the origin. HPLC: (F) Vydac 218TP15-16 $C_{18}$ RP column, 25 cm×4.6 mm, 0.1% trifluoroacetic acid, $CH_3CN$, 78:22, flow: 2.5 ml/min; (G) Vydac 218TP5 $C_4$ RP column, 25 cm×4.6 mm, 0.1% trifluoroacetic acid, $CH_3CN$, 77:23, flow: 1.0 ml/min; (H) Vydac 218TP15-16 $C_{18}$ RP column, 0.1% hexafluorobutyric acid, $CH_3CN$, 74:26, flow: 2.5 ml/min; (I) Zorbax ODS $C_{18}$ RP column, 25 cm×4.6 mm, 0.25 M triethylaminephosphate (hereinafter referred to as TEAP) (defined) buffer, pH 2.2, $CH_3CN$, 79:21, flow: 1.0 ml/min; all peptides followed at $\lambda=214$ nm.

EXAMPLE II

Preparation of

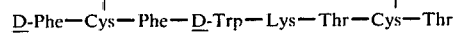

D-Phe—Cys—Phe—D-Trp—Lys—Thr—Cys—Thr t-BOC-O-Bzl-L-Threonine was esterified to the chloromethylated resin, washed, added to the reaction vessel of the automated synthesizer, deprotected, neutralized and washed, as described in Example I, except that 2.0 g (0.70 mmol) of t-BOC-O-Bzl-L-Threonine resin was used as the starting material. To 0.682 g, (2.1 mmol) $N^\alpha$-t-BOC-S-p-methylbenzyl-L-Cysteine in methylene chloride at 4° C. was added 0.29 g DCC, and the symmetrical anhydride was allowed to form for 30 minutes. The mixture was filtered into the reaction vessel and allowed to react for 30 minutes with constant shaking. Deblocking, neutralization and washing, as described in Example I, was carried out for each succeeding coupling and resulted in the desired peptide, except that t-BOC-L-Phenylalanine was used in place of protected Tyrosine at position 7. The peptide was cleaved from the resin with liquid HF, cyclized, and purified in a manner similar to that employed in Example I. Yield: 157 mg, 21%; amino acid analysis: Phe (2.07); Lys (1.00); Thr (1.90); Cys, as cysteic acid (1.88); Trp (0.87) $\epsilon\lambda=278=5500$ $M^{-1}cm^{-1}$; $[M+H]^+=1032.4$ (calc 1032.4); TLC: 0.16 (A); 0.73 (B; 0.61 (C); 0.8 (D); 0.47 (E); Paper Electrophoresis, pH 2.2 (11.2 cm); pH 5.6 (6.8 cm); HPLC, $k'=6.1$ (F); 5.1 (G); 9.2 (H); 4.0 (I); Partition Coefficient, Octanol-Water, log P=−0.77;

EXAMPLE III

Preparation of D-Phe—Cys—Phe—D-Trp—Lys—Thr—Pen—Thr

The above named compound was prepared and purified as described in Example I except that t-BOC-L-Phenylalanine was used in the synthesis instead of t-BOC-0-2,6-dichlorobenzyl-L-Tyrosine at position 7. Yield: 76 mg, 14%; amino acid analysis: Phe (1.98); Lys (1.00); Thr (1.88); Trp (0.87); Cys and Pen not determined; $[M+H]^+=1060.4$ (calc 1060.4); TLC: 0.23 (A); 0.73 (B); 0.64 (C); 0.85 (D); 0.58 (E); Paper Electrophoresis, pH 2.2 (11.2 cm); pH 5.6 (6.8 cm); HPLC, $k'=6.9$ (F); 6.0 (G); 11.5 (H); 5.4 (I); Partition Coefficient, Octanol-Water, log P=−0.71.

EXAMPLE IV

Preparation of

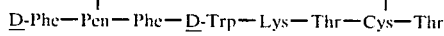
D-Phe—Pen—Phe—D-Trp—Lys—Thr—Cys—Thr

The above named compound was synthesized and purified as described in Example I using 2.0 g (0.70 mmol) t-BOC-0-Bzl-L-Threonine resin. t-BOC-S-p-methylbenzyl-L-Cysteine was attached to the Threonyl-resin instead of protected Penicillamine at position 7, t-BOC-Phenylalanine instead of protected Tyrosine, and t-BOC-S-p-methylbenzyl-L-Penicillamine replaced protected Cysteine at position 6, in this synthesis. Yield: 96 mg, 17%; amino acid analysis: Phe (1.99); Lys (1.00); Thr (1 92); Trp (0.92); Cys and Pen not determined; $[M+H]^+ = 1060.4$ (calc 1060.4); TLC: 0.25 (A); 0.74 (B); 0.64 (C); 0.85 (D); 0.58 (E); Paper Electrophoresis, pH 2.2 (11.2 cm); pH 5.6 (6.8 cm); HPLC, $k'=8.3$ (F); 7.4 (G); 12.6 (H); 6.1 (I); Partition Coefficient, Octanol Water, log $P=-0.22$.

EXAMPLE V

Preparation of

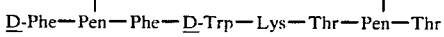
D-Phe—Pen—Phe—D-Trp—Lys—Thr—Pen—Thr

The above named compound was prepared and purified as described in Example I using 2.0 g, (0.62 mmol) (substitution of resin, 0.31 mmol/g resin) except that t-BOC-L-Phenylalanine and t-BOC-S-p-methylbenzyl-L-Penicillamine were substituted for protected Tyrosine at position 7 and Cysteine at position 6, respectively. An additional 100 ml DMF was used during the cyclization step with $K_3Fe(CN)_6$ and the partition chromatography system employed during the final purification step was butanol, water and acetic acid, 4:1:5 ($R_f=0.73$). Yield 52 mg, 7.7%; amino acid analysis: Phe (2.10); Lys (1.00); Thr (1.77); Trp (0.76); Pen, after derivatization with vinyl pyridine (2.21); $\epsilon\lambda=278= 570$ $M^{-1}cm^{-1}$; $[M+H]^+=1088.4$ (calc 1088.4); TLC: 0.29 (A); 0.75 (B); 0.64 (C); 0.60 (E); Paper Electrophoresis, pH 2.2 (11.2 cm); pH 5.6 (6.8 cm); HPLC, $k'=6.9$(F); 6.0 (G); 11.5 (H); 5.4 (I); Partition Coefficient, Octanol-Water, log $P=+0$.

EXAMPLE VI

Preparation of

D-Phe—Cys—Tyr—D-Trp—Lys—Thr—Pen—Thr—NH$_2$

A mixture of 15g polystyrene resin (Bio Beads, X-1, 200–400 mesh) in 15 ml dry (freshly distilled from $CaCl_2$) $CH_2Cl_2$ was stirred under nitrogen and 3.63 g (25.9 mmol) p-methylbenzoyl chloride was added dropwise. The mixture was stirred as the temperature was lowered to 4° C. and 3.46 g (25.9 mmol) of $AlCl_3$ was added slowly. The mixture was stirred for 2 hours at 0° C., 1.5 hours at room temperature and finally 2 hours at reflux. The reaction mixture was cooled and 500 ml of an ice/water mixture was added cautiously with stirring. After treatment with 100 ml of conc HCl, the reaction was filtered, treated with 25 ml conc HCl and filtered again. After neutralization with 0.5 M NaOH, the beads were thoroughly rinsed with a 50:50 solution of dioxane-water and dried in vacuo to constant weight. The IR spectrum (KBr pellet), showed strong absorption at 1650 cm$^{-1}$ (C=O) and 1600 cm$^{-1}$ (aromatic C=C).

A mixture of 160 ml of 88% formic acid and 200 ml of conc NH$_4$OH was heated in a 3-neck flask and the water (ca 200-210 ml) was removed by distillation until the inner temperature increased to 150°-160° C. To the hot liquid was added 5 g of the ketone resin and the mixture was stirred with an overhead stirrer for 3 days while the inner temperature was maintained at 150°-160° C. by means of an oil bath. The mixture was then cooled, filtered and thoroughly washed with dioxane-water, 1:3, methanol, CH$_2$Cl$_2$, methanol and finally CH$_2$Cl$_2$. The resin was then suspended in 0 ml conc HCl-propionic acid, 1:1 and refluxed for 10 hours. After filtration, the resin was again thoroughly washed with 10% Na$_2$CO$_3$, water-dioxane, 3:1, methanol, DMF and finally methylene chloride, dried in vacuo to constant weight to yield a cream colored material. Substitution, as determined by assaying the amount of Glycine that could be coupled to the resin, was 0.55 mmol/g resin.

t-BOC-0-Bzl-L-Threonine, 0.76 g (2.4 mmol), in methylene chloride was cooled in an ice bath and 0.26 g (1.2 mmol) DCC was added. The mixture was allowed to stand for 30 minutes and then filtered into a synthesizer vessel containing 1.5 g (0.83 mmol) NH$_2$-substituted p-methylbenzhydrylamine resin and the mixture shaken for 45 minutes. The resin was washed with methylene chloride, absolute ethanol, methylene chloride, 20 ml, 3 times each. Approximately 1 mg of resin was removed, tested with the ninhydrin solution as in Example I and found to be positive. The remaining free amino groups were then blocked by the addition of 500 mg N-acetylimidazole in dry methylene chloride for 12 hours. Resin was now negative to the ninhydrin test. Amino acid analysis gave a threonine substitution of approximately 0.46 mmol/g resin. The desired analog was prepared and purified using a procedure as described in Example I. Yield 87 mg, 12%; amino acid analysis: Phe (0.99); Tyr (0.96); Lys (1.00); Thr (1.78); Trp (0.89); Cys, as cysteic acid (1.03); Pen, not determined; $\epsilon\lambda=278=6900$ $M^{-1}cm^{-1}$; TLC: 0.24 (A); 0.70 (B); 0.64 (C); 0.85 (D); 0.52 (E); Paper Electrophoresis, pH 2.2 (11.2 cm); pH 5.6 (8.8 cm); HPLC $k'=2.9$ (F); 4.0 (G); 4.9 (H); 2.1 (I); Partition coefficient, octanol-water, log $P=-0.20$.

EXAMPLE VII

Preparation of

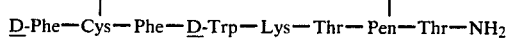
D-Phe—Cys—Phe—D-Trp—Lys—Thr—Pen—Thr—NH$_2$

The above named compound was prepared and purified as described in Example VI except that t-BOC-L-Phenylalanine was used in the synthesis instead of t-BOC-0-2,6-dichlorobenzyl-L-Tyrosine. Yield: 112 mg, 15%; amino acid analysis: Phe (2.19); Lys (1.00); Thr (2.01); Trp (0.91); Cys and Pen, not determined. TLC: 0.23 (A); 0.65 (B); 0.65 (C); 0.87 (D); 0.60 (E); Paper Electrophoresis, pH 2.2 (11.3 cm); pH 5.6 (8.7 cm); HPLC $k'=6.4$ (F); 5.8 (G); 10.5 (H); 5.2 (I); Partition coefficient, octanol-water, log $P=+0.36$.

EXAMPLE VIII

Preparation of

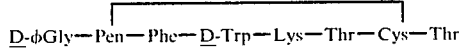

The above named compound was prepared and purified according to the procedure given in Example I except that t-BOC-S-p-methyl-benzyl-L-Cysteine was attached to the Threonyl-resin instead of the protected Penicillamine at position 11, t-BOC-S-p-methyl-benzyl-L-Penicillamine was substituted for Cysteine at position 6, t-BOC-L-Phenylalanine was substituted for Tyrosine at position 7 and t-BOC-D-Phenylglycine (t-BOC-D-φGly) was substituted for D-Phenylalanine at position 5. Yield, approximately 70 mg, ca 13%; amino acid analysis: Phe (0.94); Lys (1.00); Thr (1.99); Trp (0.76); Cys, Pen and φGly, not determined; $[M+H]^+ = 1046.4$ (calc 1046.4); TLC: 0.15 (A); 0.65 (B); 0.61 (C); 0.8 ); 0.56 (E); Paper Electrophoresis, pH 2.2 (11.2 cm); pH 5.6 (6.8 cm); HPLC, k'=5.5 (F); 4.7 (G); 8.9 (H); 3.6 (I); Partition Coefficient, Octanol-water, log $P = -0.57$.

The receptor binding bioassays are described in detail below.

Bioassay Methods

Adult Sprague-Dawly rats (150–200g) were killed by decapitation. The brain was rapidly removed and homogenized (10% wt/vol in 0.32 M sucrose in a glass homogenizer with a motor driven teflon pestle. The homogenate was then centrifuged at 43,000×g for 10 min and the resulting pellet was resuspended in 50 mM Trisma buffer (pH 7.4 at 25° C.) containing 5 mM $MgCl_2$, 2 mg/ml BSA and 20 mg/ml of bacitracin, using a Polytron homogenizer (15 sec, setting 5). The centrifugation and resuspension step was repeated once.

For all the inhibition studies, rat brain plasma membranes (100 μl) were incubated at 25° C. for 60 min in a total of 1.0 ml of 50 mM Trisma buffer containing 220,000 dpm $^{125}$I-CGP 23,996. See Czernik, A. J. and Petrack, G., *J. Biol. Chem.* 258,5525–5530 (1983) which is herein specifically incorporated by reference. 1 nM [$^3$H-]naloxone (42.3 Ci/mmol, New England Nuclear) or 1 nM [$^3$H]DADLE ([D-Ala$^2$, D-Ala$^5$]enkephalin), [$^3$H-3'5'-Tyr]DADLE, 43 Ci/mmol, New England Nuclear, and at least nine concentrations of our synthetic analogues. All incubations were done in duplicate and each compound was tested at least five times. The concentration of test compounds was determined by quantitative amino acid analysis or from published molar extinction coefficients. Specific binding to somatostatin, μ- and δ-opiate receptors was defined as the difference in the amounts of radioligands bound in the absence and presence of 1 μM somatostatin, 1 μM naltrexone, or 1 μM Met-enkephalin, respectively. The data were analyzed using nonlinear least squares regression analysis.

The compounds of the present invention were tested for their ability to inhibit electrically stimulated muscle contractions in the guinea pig ileum (GPI) assay and in the mouse vas deferens (MVD) assay. The GPI preparation has been shown to contain primarily mu-type opiate receptors and the MVD preparation primarily delta-type opiate receptors. Thus, comparisons of IC50 values in these two assay systems, as shown in Table III, provide a measure of receptor specificity of the tested analogs. Morphiceptin is a relatively selective mu opioid receptor agonist,

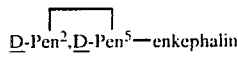

(hereinafter (DPDPE)) is a highly selective delta opioid receptor agonist. As Table 3 indicates,

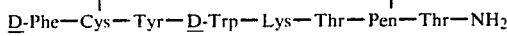

antagonized the mu agonist, morphiceptin, in the guinea pig ileum test. However, the same somatostatin analog did not antagonize DPDPE, a delta agonist, in the mouse vas deferens assay. Moreover, the somatostatin analog did not antagonize DPDPE even in a 3.3 fold higher concentration.

The tests in the guinea pig ileum were conducted as follows: strips of longitudinal muscle with adhering myenteric plexus were prepared from nonterminal ilea of guinea pigs and attached to a force transducer in a 60 ml isolated organ bath. Contractions were elicited by electrical stimulation with a Grass S44D stimulator. Morphiceptin was added in concentrations of 300 to 10,000 nM(nanomolar) to inhibit the electrically induced contractions. The inhibitory effects of morphiceptin alone and morphiceptin in the presence of the presence of 30nM somatostatin analog were determined.

The mouse vasa deferentia tests were conducted as follows: vas deferens of male mice were placed in a 60 ml tissue bath and attached to a force transducer. Contractions were induced by electrical stimulation. DPDPE was added in concentrations ranging from 1 to 300 nM to inhibit the electrically induced contractions. Percent inhibition was calculated. The inhibitory effect of DPDPE alone and DPDPE in the presence of the somatostatin analog was assessed. The somatostatin analog was tested at a concentration of 1,000 nM.

It will be apparent to those skilled in the art that various modifications and variations can be made in the processes and products of the present invention. Thus, it is intended that the present invention cover the modifications and variations of this invention provided that they come within the scope of the appended claims and their equivalents.

TABLE I

THE EFFECT OF SOMATOSTATIN AND ITS ANALOGS ON [$^3$H]NALOXONE AND [$^3$H]DADLE RECEPTOR BINDING TO RAT BRAIN HOMOGENATES

| PEPTIDE | [$^3$H]—Naloxone | | [$^3$H]—DADLE | |
|---|---|---|---|---|
| | IC$_{50}$ [nM] | n$_H$ | IC$_{50}$ [nM] | n$_H$ |
| D-Phe—Cys—Tyr—D-Trp—Lys—Thr—Pen—Thr—NH$_2$ | 3.5 | 1.02 | 952 | 0.33 |

TABLE I-continued
THE EFFECT OF SOMATOSTATIN AND ITS ANALOGS ON [$^3$H]NALOXONE AND [$^3$H]DADLE RECEPTOR BINDING TO RAT BRAIN HOMOGENATES

| PEPTIDE | [$^3$H]—Naloxone IC$_{50}$ [nM] | $n_H$ | [$^3$H]—DADLE IC$_{50}$ [nM] | $n_H$ |
|---|---|---|---|---|
| D-Phe—Cys—Phe—D-Trp—Lys—Thr—Pen—Thr—NH$_2$ | 9.9 | 1.04 | 1105 | 0.33 |
| D-Phe—Cys—Tyr—D-Trp—Lys—Thr—Pen—Thr | 293 | 1.08 | 3762 | 0.72 |
| D-Phe—Cys—Phe—D-Trp—Lys—Thr—Pen—Thr | 926 | 1.13 | 5416 | 0.83 |
| D-φGly—Pen—Phe—D-Trp—Lys—Thr—Cys—Thr | 2500 | 1.03 | 13,505 | 0.99 |
| D-Phe—Pen—Tyr—D-Trp—Lys—Thr—Cys—Thr | 471 | 1.03 | 2561 | 0.58 |
| D-Phe—Pen—Phe—D-Trp—Lys—Thr—Pen—Thr | 8266 | 1.06 | 11,066 | 0.90 |
| D-Phe—Cys—Phe—D-Trp—Lys—Thr—Cys—Thr | 2575 | 0.81 | 3139 | 0.83 |
| CGP 23,996 | >100,000 | | >100,000 | |
| D-Phe—Pen—Phe—D-Trp—Lys—Thr—Cys—Thr | 61,021 | 1.31 | 38,078 | 1.02 |
| SOMATOSTATIN | 27,361 | 1.02 | 16,369 | 1.09 |
| Ac—Phe—D-Trp—Lys—Thr | 51,468 | 1.00 | 5836 | 0.80 |

TABLE 2
INHIBITION OF $^{125}$I-CGP 23,996 BINDING TO RAT BRAIN HOMOGENATES BY SOMATOSTATIN AND ITS ANALOGS

| PEPTIDE | IC$_{50}$ (nM)* |
|---|---|
| SOMATOSTATIN | 3.3 ± 0.30 |
| CGP 23,996 | 8.3 ± 2.0 |
| D-Phe—Cys—Phe—D-Trp—Lys—Thr—Pen—Thr | 170 ± 99 |
| D-Phe—Pen—Phe—D-Trp—Lys—Thr—Cys—Thr | 400 ± 200 |
| D-Phe—Cys—Tyr—D-Trp—Lys—Thr—Pen—Thr—NH$_2$ | 690 ± 220 |
| D-Phe—Pen—Phe—D-Trp—Lys—Thr—Pen—Thr | 800 ± 300 |
| D-Phe—Cys—Phe—D-Trp—Lys—Thr—Cys—Thr | 980 ± 680 |
| D-Phe—Cys—Phe—D-Trp—Lys—Thr—Pen—Thr—NH$_2$ | 1500 ± 470 |
| D-Phe—Cys—Tyr—D-Trp—Lys—Thr—Pen—Thr | 1600 ± 460 |
| D-Phe—Pen—Tyr—D-Trp—Lys—Thr—Cys—Thr | 4000 ± 780 |
| Ac—Phe—D-Trp—Lys—Thr | 7100 ± 870 |

*Inhibition of $^{125}$I-labeled CGP 23,996 (des Ala$^1$, Gly$^2$—desamino-Cys$^3$—[Tyr$^{11}$]—dicarba$^{3,14}$-somatostatin.

TABLE 3
SELECTIVE MU OPIOID RECEPTOR ANTAGONISM

| | Guinea pig ileum test: | | | | |
|---|---|---|---|---|---|
| Concentration of morphiceptin: | 300 | 1000 | 3000 | 10000 | nM |

TABLE 3-continued

| SELECTIVE MU OPIOID RECEPTOR ANTAGONISM | | | | | | |
|---|---|---|---|---|---|---|
| Percent inhibition of contractions* | | | | | | |
| Morphiceptin alone | 28 ± 3 | 58 ± 3 | 73 ± 4 | 73 ± 3 | | |
| Morphiceptin plus 300 nM | 7 ± 2 | 18 ± 3 | 43 ± 6 | 62 ± 2 | | |

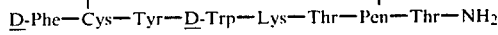
D-Phe—Cys—Tyr—D-Trp—Lys—Thr—Pen—Thr—NH₂

| | Mouse vas deferens test: | | | | | | |
|---|---|---|---|---|---|---|---|
| Concentration of DPDPE | 1 | 3 | 10 | 30 | 100 | 300 | nM |
| Percent inhibition of contractions* | | | | | | | |
| DPDPE alone | 6 ± 1 | 11 ± 3 | 22 ± 6 | 42 ± 9 | 53 ± 9 | 77 ± 8 | |
| DPDPE plus 1000 nM | 13 ± 3 | 28 ± 4 | 48 ± 8 | 73 ± 9 | 91 ± 5 | 97 ± 1 | |

D-Phe—Cys—Tyr—D-Trp—Lys—Thr—Pen—Thr—NH₂

*Each value is the mean ± standard error of experiments carried out in 2–16 preparations.

What is claimed is:

1. A polypeptide having the formula:

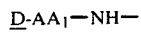
D-AA₁—NH—

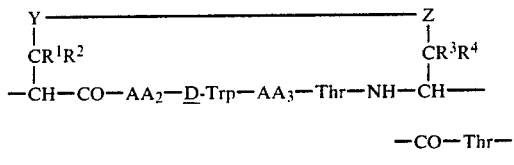

wherein
X is CONH₂ or CH₂OH;
Y and Z are independently sulfur or CH₂;
R¹ and R², which may be the same or different, are hydrogen, methyl, ethyl, cyclopentamethylene, or a lower alkyl group having five or less carbon atoms;
R³ and R⁴, which may be the same or different, are hydrogen, methyl, ethyl, cyclopentamethylene, or a lower alkyl group having five or less carbon atoms, provided, however, that R¹, R², R³, and R⁴ may not all be hydrogen;
AA₁ is Phe, D-Phe, phenyl-Gly, D-phenyl-Gly, Tyr, D-Tyr, L-1-Naphthylalanine, D-1-Naphthylalanine, or D-Phe(4-Me);
AA2 is Tyr, Phe, Tyr(OMe), Phe(4-Me), Tyr(OEt), or Phe(4-Et); and
AA₃ is Lys, Arg, Orn or homo-Arg.

2. A polypeptide according to claim 1 having the formula:

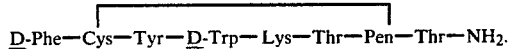
D-Phe—Cys—Tyr—D-Trp—Lys—Thr—Pen—Thr—NH₂.

3. A polypeptide according to claim 1 having the formula:

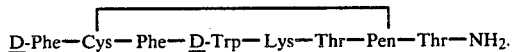
D-Phe—Cys—Phe—D-Trp—Lys—Thr—Pen—Thr—NH₂.

4. A polypeptide according to claim 1 having the formula:

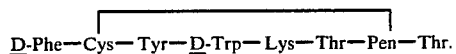
D-Phe—Cys—Tyr—D-Trp—Lys—Thr—Pen—Thr.

5. A polypeptide according to claim 1 having the formula:

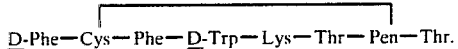
D-Phe—Cys—Phe—D-Trp—Lys—Thr—Pen—Thr.

6. A polypeptide according to claim 1 having the formula:

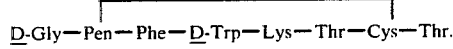
D-Gly—Pen—Phe—D-Trp—Lys—Thr—Cys—Thr.

7. A polypeptide according to claim 1 having the formula:

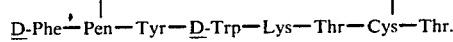
D-Phe—Pen—Tyr—D-Trp—Lys—Thr—Cys—Thr.

8. A polypeptide according to claim 1 having the formula:

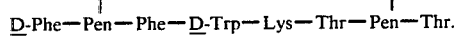
D-Phe—Pen—Phe—D-Trp—Lys—Thr—Pen—Thr.

9. A compound according to claim 1 wherein either R¹ and R² both methyl or R³ and R⁴ are both methyl.

10. A compound according to claim 1 wherein said compound is a mu receptor antagonist.

11. A process for treating irritable bowel disease comprising administering a safe and effective amount of an opioid receptor antagonist of claim 10.

12. A process for ameliorating opioid effects in humans and other mammals comprising administering a safe and effective amount of an opioid receptor compound of claim 1.

13. A process for treating digestive diseases in humans and other mammals comprising administering a safe and effective amount of an opioid receptor compound of claim 1.

14. The process of claim 12 wherein said opioid effects are opiate addiction, constipation or, respiratory depression.

15. A pharmaceutical composition comprising an effective amount of an opioid receptor antagonist having enhanced specificity for the mu opioid receptors of the formula:

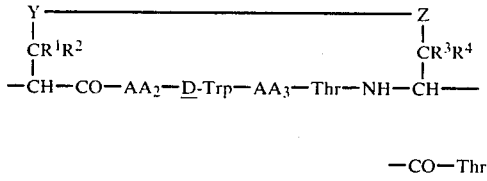

wherein

X is $CONH_2$ or $CH_2OH$;

Y and Z are independently sulfur or $CH_2$;

$R^1$ and $R^2$, which may be the same or different, are hydrogen, methyl, ethyl, cyclopentamethylene, or a lower alkyl group having five or less carbon atoms;

$R^3$ and $R^4$, which may be the same or different, are hydrogen, methyl, ethyl, cyclopentamethylene, or a lower alkyl group having five or less carbon atoms, provided, however, that $R^1$, $R^2$, $R^3$, and $R^4$ may not all be hydrogen;

$AA_1$ is Phe, D-Phe, phenyl-Gly, D-phenyl-Gly, Tyr, D-Tyr, L-1-Naphthylalanine, D-1-Naphthylalanine, or D-Phe(4-Me);

$AA_2$ is Tyr, Phe, Tyr(OMe), Phe(4-Me), Tyr(OEt), or Phe(4-Et); and $AA_3$ is Lys, Arg, Orn or homo-Arg or a pharmaceutically acceptable salt thereof, in a pharmaceutically acceptable carrier.

16. The pharmaceutical composition of claim 15 wherein $R1$ and $R^2$ are hydrogen and $R^3$ and $R^4$ are methyl.

* * * * *